United States Patent [19]
Markgraaf

[11] Patent Number: 5,715,850
[45] Date of Patent: Feb. 10, 1998

[54] PERSONAL EAR CLEANING DEVICE

[75] Inventor: Etienne G. Markgraaf, Sandton, South Africa

[73] Assignee: Toddling Products (Proprietary) Limited, South Africa

[21] Appl. No.: 651,086

[22] Filed: May 22, 1996

[30] Foreign Application Priority Data

May 28, 1995 [ZA] South Africa .......................... 95/4200

[51] Int. Cl.⁶ .................................................. A45D 44/00
[52] U.S. Cl. ........................... 132/333; 606/162; 606/161
[58] Field of Search ............................. 132/333; 606/162, 606/161; 604/54, 48, 1, 2, 3, 289; 128/757, 758

[56] References Cited

U.S. PATENT DOCUMENTS

| | | | |
|---|---|---|---|
| 3,110,304 | 11/1963 | Hartman | 606/160 |
| 3,259,128 | 7/1966 | Leight | 128/865 |
| 5,209,757 | 5/1993 | Krug et al. | 606/162 |
| 5,334,212 | 8/1994 | Karell | 606/162 |
| 5,374,276 | 12/1994 | Lay | 606/162 |
| 5,509,921 | 4/1996 | Karell | 606/162 |

*Primary Examiner*—Cary E. O'Connor
*Assistant Examiner*—Pedro Philogene

[57] ABSTRACT

This invention relates to an ear cleaning device in the form of an elongate member having a collecting formation at one end and a handle at its opposite end. A stop formation is located intermediate the handle and the collecting formation. Intermediate the stop formation and the collecting formation is a resiliently deformable, soft plug of cleaning material for engaging and cleaning the ear surface in the region of the entrance to the ear canal.

16 Claims, 2 Drawing Sheets

PERSONAL EAR CLEANING DEVICE

FIELD OF THE INVENTION

This invention relates to a personal ear cleaning device which is capable of being used safely by a person to clean his own ears as and when required. More particularly, the invention relates to an ear cleaning device of the general type described in my earlier patent 83/6818.

BACKGROUND TO THE INVENTION

In my said earlier patent 83/6818 I described and claimed an ear cleaning device which simply comprised an operative end for insertion into the ear passage or canal to collect wax or other dirt therein; a manipulating handle whereby the equipment may be held; and means whereby the introduction of the elongate device was limited to a depth insufficient to cause damage to the eardrum and, in fact, whereby the operative end is maintained a safe distance away from the eardrum. Such means are most conveniently a stop suitably positioned intermediate the operative and handle ends of the device.

A drawback of the ear cleaning device described in my earlier patent is that no means is provided for cleaning the outer regions of the ear canal so that, even after cleaning using that device, wax or other dirt can remain at the entrance to the ear canal, or a short distance inwardly therefrom, which may be unsightly.

OBJECT OF THE INVENTION

It is an object of the present invention to overcome this disadvantage.

SUMMARY OF THE INVENTION

In accordance with this invention there is provided an ear cleaning device comprising an elongate member formed at one end, the operative end, with a collection formation; at the opposite end with a handle or finger grip; a stop formation intermediate the ends of the elongate member adapted to limit the extent to which the operative end can be inserted into an ear canal; and, positioned between the stop formation and the collection formation, a resiliently deformable, soft plug of cleaning material for engaging and cleaning the ear surface in the region of the entrance to the ear canal.

Further features of the invention provide for the plug of cleaning material to be made of a material selected from the group comprising foam plastic or rubber material, cottonwool, or a mat of suitable fibers optionally bonded to each other to form the plug of material; for the shape of the plug of material to be selected from part-spherical, truncated conical, truncated conical with concave sides, or ellipsoidal, optionally with deep grooves formed in the surface of the solid shape for collecting wax or other dirt; for the collection formation to be defined by at least one loop (a first loop) located at the end of the elongate element with an optional second loop orientated at an angle to the first loop in each of which cases the remote end or ends of the loop or loops may be indented, alternatively the collection formation is defined by at least one arcuate scraper (a first scraper) located at the end of the loop or loops may be indented, alternatively the collection formation is defined by at least one arcuate scraper (a first scraper) located at the end of the elongate element with an optional second scraper oriented at an angle to the first loop; for the stop to be located at a distance from the extreme operative end of the collection formation equal to approximately one half of the distance between the entrance to the ear canal and the eardrum of an average person; and, for the elongate device itself to be injection molded from soft, resiliently deformable, plastics material.

Preferably, the stop formation assumes the form of a disc, conveniently a dished disc, such that a smooth part-spherical surface is presented to the entrance to the ear canal. Also, a region of the handle is preferably substantially circular in cross-section and suitably knurled or otherwise roughened to enable the device to be rotated, such as between a forefinger and thumb.

In order that the invention may be fully understood various different embodiments thereof will now be described with reference to the accompanying drawings.

DETAILED DESCRIPTION OF THE DRAWINGS

Figure 1:
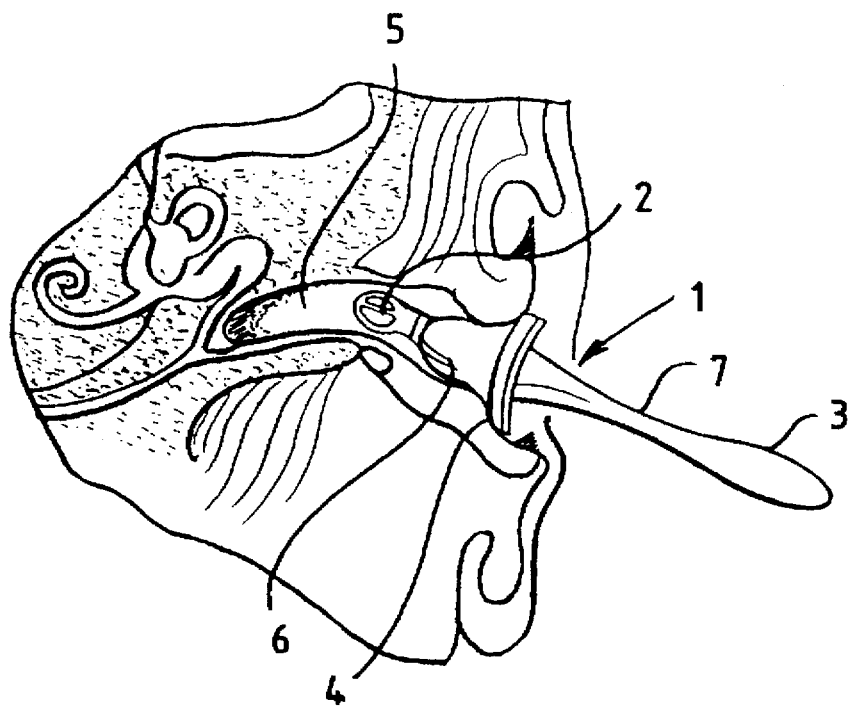
FIG. 1 is a schematic elevation illustrating an ear cleaning device according to the invention in the operative position in an ear canal.

As described in my said earlier patent, and as illustrated most clearly in FIG. 1, the general principles of the invention are that an ear cleaning device comprises an elongate member (1) having, at one end thereof, an operative collection formation (2) and, at the opposite end, a handle (3). A convex stop (4) is located intermediate the ends and is positioned such that the collection formation (2) can only enter the ear canal (5) to the extent of about one half of the length thereof. This is considered to be adequate for the removal of most wax deposits and the like. The convex stop (4) is arranged to prevent further insertion of the device as shown clearly in FIG. 1.

As provided by this invention there is interposed between the stop (4) and the collection formation (2), a plug (6) of cleaning material which may, as indicated above, be a foam plastic material or a matted fibrous material whereof the fibres are preferably stuck together and spaced apart considerably to provide a porous nature to the plug. The plug may also be made of cottonwool if required.

Figure 2:
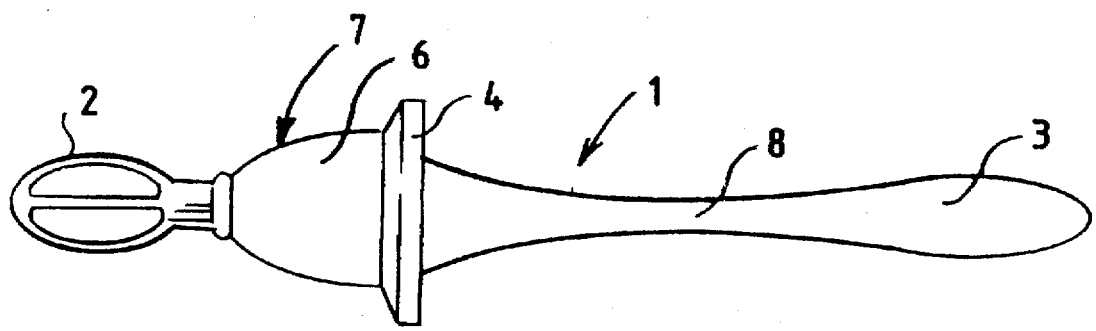
FIG. 2 is an enlarged elevation illustrating one embodiment of the invention.

The outer surface (7) of the plug may have a variety of different shapes one of which is shown in FIG. 2. In this case the shape is simply an elongate, convex plug tapering downwardly from the stop towards the collection formation (2).

Finally, the central region (8) of the handle is of reduced diameter and knurled or otherwise roughened so that it can be twirled between a finger and thumb for example.

In use, it will be understood that the ear cleaning device is held by the handle and the operative wax collection formation inserted into the ear canal until such time as the stop engages the outer ear. At this stage the cleansing plug (6) will lightly engage the entrance to the ear canal for a short distance from said entrance.

The element is then manipulated using the handle, and twirled as required, so that wax can be collected in the collection formation (2) and, simultaneously, the outer region and entrance to the ear canal is cleaned by means of the plug.

Figure 3A:
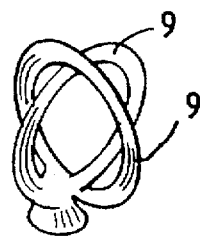
FIG. 3 a, b, c, d and e each illustrate, in isometric view, a different form of operative end or collection formation which is regarded as being suitable for implementing the invention.

The actual configuration of the collection formation may vary widely. Five different proposals are illustrated in FIGS. 3a, b, c, d and e respectively. In the case of the variation illustrated in FIG. 3a, two substantially circular shaped loops (9), each located in a plane including the axis of the cleaning device, but angularly offset at 90° to each other, are provided. These loops are resiliently deformable and, as with the remainder of the element, made of soft injection molded plastics material such as SANTOPRENE® a registered trademark of Monsanto Company exclusively licensed to Advanced Elastomer Systems, L.P. for thermoplastic rubber marketed by Advanced Elastomer Systems, L.P. of Akron, Ohio.

Figure 3B:
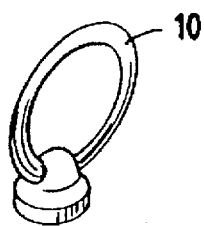
Figure 3C:
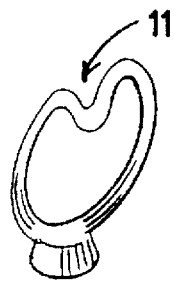

It is also within the scope of this invention that a single circular loop (10) be used as illustrated in FIG. 3b. The free end of the loop may also be indented as indicated by numeral 11 in FIG. 3c.

Figure 3D:
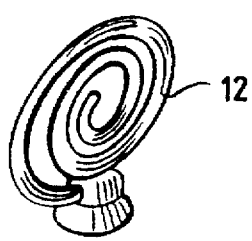

It may be that a spiral formation such as is indicated by numeral 12 in FIG. 3d, will be desirable because, in such a case, cleaning of the collection formation is very much facilitated as it can simply be drawn through a cloth or wad of cottonwool to remove wax therefrom.

Figure 3E:
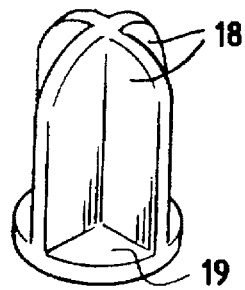

As an alternative to the hollow centered loops described in FIGS. 3a to d, arcuate scrapers (18) can be used as shown in FIG. 3e. In this embodiment two such scrapers (18) are located in a plane including the axis of the cleaning device and are angularly offset at 90° to each other. The scrapers (18) are solid and project from a discoid base (19).

Figure 4A:
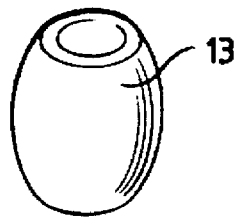
FIG. 4 a, b and c illustrate three alternative forms of cleaning plug for installation between the stop and collection formation.
Figure 4B:
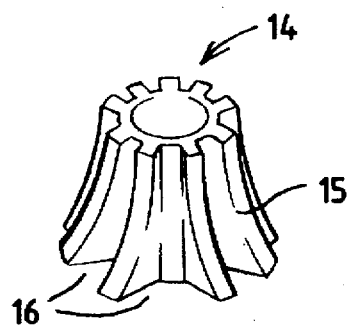

FIGS. 4a, b and c illustrate three different shapes of plug which can be used. FIG. 4a illustrates a truncated ellipsoidal shape of plug (13). FIG. 4b illustrates a truncated conical shaped plug with concave sides as illustrated by numeral 15. This figure also illustrates the concept of having grooves (16) extending deep into the plug and providing space for accommodating wax of other dirt removed by the plug during use.

Figure 4C:
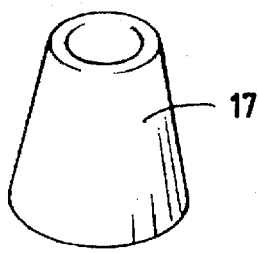

FIG. 4c illustrates a simple truncated conical shaped plug (17).

It will be understood that numerous variations may be made to the embodiments of the invention described above without departing from the scope hereof. In particular, the collection formation and portion of the elongate element passing through he plug 14 may be made removable from the handle in order to provide disposable end pieces. The product itself may be made either as a disposable product or as a more elaborate re-usable product. The exact shape and configuration of the collection formation may be varied widely as can the shape of the plug and the material from which it is made.

I claim:

1. An ear cleaning device comprising an elongate member formed at one end having an operative end with a collection formation, and an opposite end with a handle; a stop formation intermediate the ends of the elongate member adapted to limit the extent to which the operative end can be inserted into an ear canal; and, positioned between the stop formation and the collection formation, a resiliently deformable, soft plug of cleaning material for engaging and cleaning the ear surface in the region of the entrance to the ear canal.

2. An ear cleaning device as claimed in claim 1 in which the plug of cleaning material is made of a material selected from the group consisting of foam plastic, rubber material, cottonwool, or a mat of suitable fibres.

3. An ear cleaning device as claimed in claim 2 in which the material from which the plug of cleaning material is made is bonded to form the plug of material.

4. An ear cleaning device as claimed in claim 3 in which the shape of the plug of material is selected from the group consisting of part-spherical, truncated conical, truncated conical with concave sides, or ellipsoidal.

5. An ear cleaning device as claimed in claim 4 in which deep grooves are formed in the surface of the solid shape.

6. An ear cleaning device as claimed in claim 1 in which the collection formation is defined by at least one loop located at the end of the elongate member.

7. An ear cleaning device as claimed in claim 6 in which the collection formation has a second loop orientated at an angle to said at least one loop.

8. An ear cleaning device as claimed in claim 7 in which said at least one loop is equipped with an indentation adjacent said operative end.

9. An ear cleaning device as claimed in claim 1 in which said collection formation is defined by at least one arcuate scraper located at said operative end of the elongate member.

10. An ear cleaning device as claimed in claim 9 in which said collection formation has a second arcuate scraper orientated at an angle said at least one arcuate scraper.

11. An ear cleaning device as claimed in claim 1 in which the stop is located at a distance from the operative end of the elongate member equal to approximately one half of the distance between the entrance to the ear canal and the eardrum of an average person.

12. An ear cleaning device as claimed in claim 1 in which the elongate member is injection molded from soft, resiliently deformable, plastics material.

13. An ear cleaning device as claimed in claim 12 in which said plastics material is a thermoplastic rubber.

14. An ear cleaning device as claimed in claim 1 in which said stop formation assumes the form of a disc.

15. An ear cleaning device as claimed in claim 14 in which said disc is dished such that a smooth part-spherical surface is presented to the entrance to the ear canal.

16. An ear cleaning device as claimed in claim 1 in which a region of the handle is substantially circular in cross-section and suitably knurled to enable the device to be rotated, such as between a forefinger and thumb.

* * * * *